United States Patent [19]

Zahler et al.

[11] Patent Number: 4,855,466
[45] Date of Patent: Aug. 8, 1989

[54] PURINYL CYCLOBUTANES

[75] Inventors: Robert Zahler; Glenn A. Jacobs, both of Princeton, N.J.

[73] Assignee: E. R. Squibb & Sons, Inc., Princeton, N.J.

[21] Appl. No.: 138,737

[22] Filed: Dec. 28, 1987

[51] Int. Cl.$^4$ ............................................. C07D 303/00
[52] U.S. Cl. .................................... 549/546; 544/244; 544/265; 544/277; 544/264; 549/215
[58] Field of Search ................................ 549/546, 215

[56] References Cited

U.S. PATENT DOCUMENTS 4,543,255  9/1985  Shealy et al. ........................ 549/546

FOREIGN PATENT DOCUMENTS 159264   10/1985  European Pat. Off. ............ 549/546
0182315   5/1986  European Pat. Off. ............ 549/546
0184473   6/1986  European Pat. Off. ............ 549/546
0219838   4/1987  European Pat. Off. ............ 549/546

OTHER PUBLICATIONS

Hoshino et al., Inhibition of Infectivity of Human Immunodifficiency Virus by Oxetanocin, J. Antibiotics, 40(7), 1077 (1987).
Shimada et al., Oxetanocin, A Novel Nucleoside From Bacteria, J. Antibiotics, 39(11), 1623 (1986).
Shealy et al., Synthesis and Antiviral Activity of Carbocyclic Analogues of 2'-Deoxyribofuranosides of 2-Amino-6-substituted-purines and of 2-Amino-6--substituted-8-azapurines, J. Med. Chem., 27, 1416 (1984).
Secrist et al., Resolution of Racemic Carbocyclic Analogues of Purine Nucleosides through the Action of Adenosine Deaminase, Antiviral Activity of the Carbocyclic 2'-Deoxyguanosine Enantiomers, J. Med. Chem., 30, 746 (1987).
Canning et al., Synthesis and Antiviral Activity of 9-[-CIS]-2-[Hydroxymethyl)-Cyclopropmethyl] Guanine and Related Compounds, ACS National Meeting, 1986 (Abstract No. 33).
Nakamura, et al., The X-Ray Structure Determination of Oxetanocin, J. Antibiotics, 39, 1626-1629 (1986).
Niitsuma, et al., Studies on the Total Synthesis of Oxetanocin; I. The First Synthesis of a Nucleoside Having Oxetanosyl-N-Glycoside, Tetrahedron Letters, 28, 3967-3970 (1987).
Niitsuma, et al., Studies on the Total Synthesis of Oxetanocin; II. Total Synthesis of Oxetanocin; Tetrahedron Letters, 28, 4713-4714 (1987).
Austin, et al., Chiral Oxetanes From Sugar Lactones: Synthesis of Derivatives of 3,5-Anhydro-1,2-O-Isopropylidene- -D-Glucuronic Acid and of 3,5-Anhydro-1,2-O-Isopropylidene-B-L-Iduronic Acid, Tetrahedron Letters, 28, 4741-4744 (1987).
Shimada et al., Derivatives of Oxetanocin: Oxetanocins H, X and G, and 2-Aminooxetanocin A, J. Antibiotics, 40, 1788-1790 (1987).
Derwent Abstract No. 87-296034/42 of Japanese Specification JP-048499 published Sep. 12, 1987.

Primary Examiner—Mary C. Lee
Assistant Examiner—J. Richter
Attorney, Agent, or Firm—Donald J. Barrack; Stephen Venetianer

[57] ABSTRACT

Disclosed are compounds having the formula

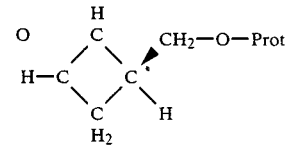

wherein Prot is a hydroxyl protecting group.

The compounds are useful as intermediates in the preparation of compounds of the formula

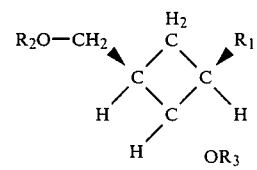

which in turn are useful as antiviral agents.

1 Claim, No Drawings

PURINYL CYCLOBUTANES

BRIEF DESCRIPTION OF THE INVENTION

Antiviral activity is exhibited by compounds having the formula

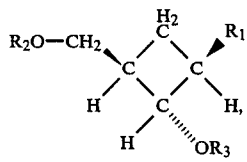

and pharmaceutically acceptable salts thereof. In formula I, and throughout the specification, the symbols are as defined below.

$R_1$ is

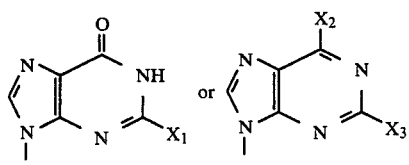

wherein $X_1$, $X_2$ and $X_3$ is independently hydrogen or amino, with the proviso that if $X_2$ is hydrogen, $X_3$ is amino;

$R_2$ is hydrogen, —$PO_3H_2$ or

wherein $X_4$ is alkyl, substituted alkyl, aryl; and
$R_3$ is hydrogen or

with the proviso that when $R_2$ is —$PO_3H_2$, $R_3$ is hydrogen and when $R_3$ is

$R_2$ is

Listed below are definitions of terms used to describe the compounds of this invention. These definitions apply to the terms as they are used throughout the specification (unless they are otherwise limited in specific instances) either individually or as part of a larger group.

The term "acyl" refers to phenyl and phenyl substituted with one, two or three substituents. Preferred substituents are alkyl of 1 to 6 carbons, alkoxy of 1 to 6 carbons, halogen, trifluoromethyl, amino, alkylamino, dialkylamino, nitro, cyano, alkanoyloxy of 2 to 11 carbons, carboxy, carbamoyl and hydroxy.

The term "alkyl" refers to both straight and branched chain groups. Those groups having 1 to 10 carbon atoms are preferred.

The term "substituted alkyl" refers to alkyl groups having one, or more, substituents. Preferred substituents are halogen, amino, azido, hydroxy, cyano, trialkylammonium wherein each alkyl group has 1 to 6 carbons, alkoxy of 1 to 6 carbons, aryl and carboxy.

DETAILED DESCRIPTION OF THE INVENTION

The cyclobutanes of formula I, and the pharmaceutically acceptable salts thereof, are antiviral agents that can be used to treat viral infections in mammalian species such as domesticated animals (e.g., dogs, cats, horses and the like) and humans, and avian species (e.g., chickens and turkeys). They are effective against herpes simplex virus 1 and 2, varicella-zoster virus, cytomegalovirus, and vaccinia virus. They may also be effective against a variety of DNA and RNA viruses. Exemplary DNA viruses in addition to those named above include herpes viruses (e.g., Epstein-Barr virus, pseudorabies virus, and the like), other poxviruses (e.g., monkey pox and myxoma), papovaviruses (e.g., the papilloma viruses), hepatitis B virus, and adenoviruses. Exemplary RNA viruses are the retroviruses (e.g., human immunodeficiency viruses), rotaviruses, influenza viruses, paramyxovirsues, and picornoviruses such as the rhinoviruses. The compounds of this invention may be administered parenterally (for example, by intravenous, intraperitoneal or intramuscular injection), orally, or topically depending on whether the preparation is used to treat internal or external viral infections.

For internal infections, the compounds may be administered orally or parenterally in an amount effective to treat the infection. The dosage will, of course, depend on the severity of the infection, but will likely be in the range of about 1.0 to 30 mg/kg of body weight.

For infections of the eye, or other external tissues, e.g., mouth and skin, the compositions may be applied to the infected part of the body of the patient topically as an ointment, cream, aerosol, gel, powder, lotion, suspension or solution (e.g., as eye drops). The concentration of the compound in the vehicle will, of course, depend on the severity of the infection, but will likely be in the range of about 0.1 to 7% by weight.

The compounds of this invention can be prepared from the known chemical compound 1-chloro-3-(hydroxymethyl)cyclobutane, which is a mixture of cis and trans isomers. Its hydroxymethyl group is first protected using, for example, a silyl containing group (e.g., t-butyldiphenylsilyl), trityl, substituted trityl (e.g., 4,4'-dimethoxytrityl), or benzyl protecting group. The protection reaction yields a compound of the formula

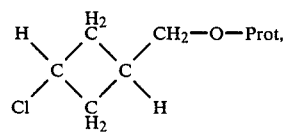

wherein "Prot" stands for a protecting group; i.e., a group that protects the hydroxyl group from involvement in subsequent reactions. This protected cyclobutane is a mixture of cis and trans isomers.

Protection with a benzyl group can be accomplished by treating 1-chloro-3-(hydroxymethyl)cyclobutane with sodium hydride in the presence of benzyl bromide in a polar aprotic solvent such as dimethylformamide, dimethylsulfoxide or tetrahydrofuran. Protection with a t-butyldiphenylsilyl group can be accomplished by treating a dimethylformamide solution of 1-chloro-3-(hydroxymethyl)cyclobutane with t-butyldiphenylsilyl chloride in the presence of imidazole. Protection with a trityl or substituted trityl group can be accomplished by (i) treating a pyridine solution of 1-chloro-3-(hydroxymethyl)cyclobutane with trityl chloride or substituted trityl chloride, (ii) treating a dimethylformamide solution of 1-chloro-3-(hydroxymethyl)cyclobutane with trityl chloride or substituted trityl chloride in the presence 4-N,N-dimethylaminopyridine or (iii) treating a dichloromethane solution of 1-chloro-3-(hydroxymethyl)cyclobutane with trityl chloride or substituted trityl chloride in the presence of triethylamine.

Basic elimination of hydrogen chloride from a compound of formula II using a base such as potassium t-butoxide in a polar aprotic solvent, such as dimethylsulfoxide or tetrahydrofuran yields the corresponding compound having the formula

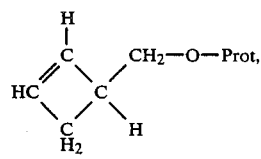

III as a racemic mixture. Alternatively, a base such as lithium diisopropylamide in a solvent such as tetrahydrofuran can be used to effect the elimination.

Epoxidation of a compound of formula III using a peracid, such as m-chloroperoxybenzoic acid yields the corresponding compound having the formula

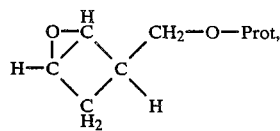

IV as a racemic mixture of cis and trans diastereomers. Separation of the diastereomers using conventional methodology provides the desired trans stereoisomer having the formula

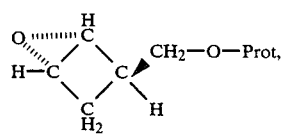

V as a racemic mixture. Alternatively, preferential formation of the trans epoxide can be achieved by treating a methanol solution of a compound of formula III with benzonitrile/30% hydrogen peroxide in the presence of a buffer (e.g., potassium bicarbonate or monobasic potassium phosphate/sodium hydroxide).

Nucleophilic substitution on the epoxide of a compound of formula V using a nucleophile of the formula $R_1'$—H, wherein $R_1'$ is

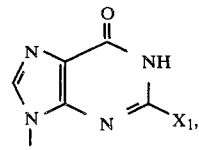

VI

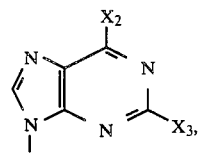

VII or a protected form of a purine base of formula VI or VII, can be accomplished in the presence of a base, such as sodium hydride or potassium carbonate, in a polar aprotic solvent such as dimethylformamide or sulfolane. A complexing agent such as 18-crown-6 ether or 15-crown-5 ether canbe used in conjunction with the sodium hydride or potassium carbonate to facilitate nucleophilic substitution on the epoxide. The resulting compound has the formula

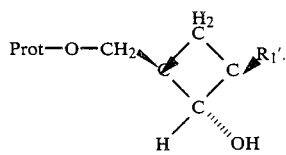

VIII

Removal of the one, or more, protecting groups from a compound of formula VIII can be accomplished using art-recognized procedures which will depend, of course, on the particular protecting group or groups present, and yields the products of formula I wherein $R_2$ and $R_3$ are hydrogen.

Alternatively, compounds of formula I wherein $R_1$ is

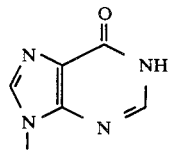

can be prepared by treating the corresponding compound of formula I wherein $R_1$ is

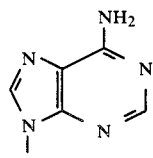

with adenosine deaminase or nitrous acid.

The compounds of formula I wherein $R_2$ is

and R₃ is hydrogen or

can be prepared from the corresponding alcohols using conventional acylation techniques. Compounds of formula V wherein R₂ is —PO₂H₂ (and R₃ is hydrogen) can be prepared from the corresponding alcohols using conventional phosphorylation techniques.

The compounds of formula I wherein R₂ and/or R₃ are hydrogen or

can form acid-addition salts with inorganic and organic acids. Illustrative are the hydrohalide (e.g., hydrochloride and hydrobromide), alkylsulfonate, sulfate and phosphate salts. The compounds of formula I wherein R₂ is —PO₃H₂ can form basic salts with inorganic and organic bases. Illustrative are alkali metal salts (e.g., sodium and potassium), alkaline earth metal salts (e.g., calcium and magnesium), ammonium and substituted ammonium salts.

Those compounds of formula I wherein R₁ is

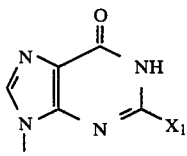

exist in a tautomeric equilibrium as shown below:

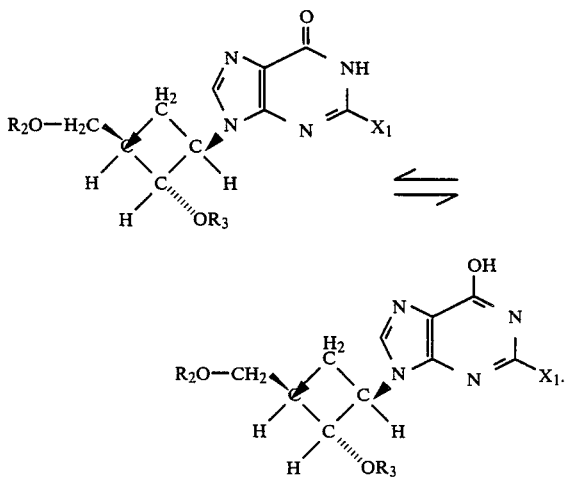

Both of these tautomeric forms are encompassed within the structural formula I.

The stereochemistry shown for the compounds of this invention is relative, not absolute. It is drawn to show that in the compounds of this invention, the purine base (R₁) is cis with respect to the —CH₂—OR₂ substituent and trans with respect to the OR₃ substituent.

The following examples are specific embodiments of this invention.

EXAMPLE 1

(1α,2β,3α)-9-[2-Hydroxy-3-(hydroxymethyl)cyclobutyl]guanine (A) [[(3-Chlorocyclobutyl)methoxy]methyl]benzene A mixture of 3-chlorocyclobutanemethanol (17.3 g, 0.143 mole) and benzylbromide (29.96 g, 0.1576 mole) in dry dimethylformamide (123 ml) was stirred at room temperature under an argon atmosphere and a 60% suspension of sodium hydride (6.31 g) was added. The reaction was stirred at ambient temperature for 22.5 hours. The reaction mixture was poured into 600 ml of water and the aqueous mixture extracted with ethyl acetate (4×500 ml). The ethyl acetate extracts were combined and dried over anhydrous sodium sulfate and the ethyl acetate evaporated in vacuo yielding the crude product as a yellow oil. The material was purified on a 2-liter Merck silica gel column eluting with 3 liters of hexane, followed by 5% ethyl acetate/hexane. The fractions containing the desired product were combined and the volatiles evaporated in vacuo yielding 28.6 g of the title compound as a pale yellow oil.

(B) [(2-Cyclobuten-1-ylmethoxy)methyl]benzene

[[(3-Chlorocyclobutyl)methoxy]methyl]benzene (82 g, 0.39 mole) in 390 ml of dry dimethylsulfoxide was slowly added to a solution of potassium t-butoxide (132 g, 1.17 mole) in 390 ml of dry dimethylsulfoxide in a water-bath at 18° C. under a dry argon atmosphere. After stirring for 1 hour at room temperature, the reaction mixture was poured into 1600 ml of water and extracted with ether (3×1000 ml). The ether extracts were back-extracted with water (4×2000 ml) and the ether extract was then dried over sodium sulfate. The ether was removed in vacuo and the crude product was purified on a Merck silica column, eluting the column with 5% ethyl acetate-hexane. Appropriate fractions were combined and the solvents removed in vacuo yielding 60.0 g of the title compound as a colorless liquid.

(C)

(1α,2α,4α)-2-[(Phenylmethoxy)methyl]-5-oxabicyclo[2.1.0]pentane

A solution of 80% m-chloroperoxybenzoic acid (19.0 g, 0.088 mol) in 600 ml of dichloromethane was cooled to 0° C. and a solution of [(2-cyclobuten-1-ylmethoxy)-methyl]benzene (14.0 g, 0.080 mol) was added and the resulting mixture was stirred overnight at 5° C. under an argon atmoshere. The precipitated m-chlorobenzoic acid was removed by filtration and the dichloromethane solution was washed with 5% sodium thiosulfate (1×500 ml), saturated sodium bicarbonate (3×500 ml) followed by washing with water (2×500 ml) and then dried over anhydrous sodium sulfate. The solution was filtered and the dichloromethane was evaporated in vacuo yielding 11.6 g of a 1:1 mixture of cis and trans product.

A quantity of the cis and trans isomers (1:1) were separated by preparative HPLC using a "Water's Prep 500" with a 500 ml silica gel column eluting with 2.5% ethyl acetate/hexane loading 2 g of mixture at 100 ml/minute and then eluting the column at a flow rate of 200 ml/minute (total 10 g of mixture used). Peak shaving technique was used to enrich one isomer over the other, with the mixture being recycled through the column 3 times. A total of 2.1 g of trans epoxide and 2.48 g of cis epoxide was separated.

Alternative Separation of Cis and Trans Isomers

A crude mixture of cis and trans epoxide (1:1, 58 g) was isolated from two separate m-chloroperoxybenzoic acid oxidations of two 27.05 batches of [(2-cyclobuten-1-ylmethoxy)methyl]benzene following the general procedures described above. Two equal 29 g portions were purified on two separate 3.5 liter silica gel columns eluting with 5% ethyl acetate/pentane. The fractions containing essentially pure (1α,2α,4α)-2-[(phenylmethoxy)methyl]-5-oxabicyclo[2.1.0]pentane were combined and the solvents removed in vacuo yielding 4.02 g of desired compound. Those fractions containing a greater than 1:1 ratio of trans epoxide were combined and the solvents removed in vacuo yielding 20.5 g of a mixture enriched in trans epoxide.

The trans-enriched mixture was further purified by preparative HPLC using a "Waters Prep 500" equipped with two tandem 500 ml silica gel columns eluting with 5% ethyl acetate/pentane loading 4 g of the mixture at a time (at a flow rate of 250 ml/minute). A total of 20.5 g of material was loaded in this fashion. Peak shaving technique was used to enrich one isomer over the other, with the mixture being recycled back through the column once. Eventually, 6.91 g of essentially pure (1α,2α,4α)-2-[(phenylmethoxy)methyl]-5-oxabicyclo[2.1.0]pentane was isolated in this fashion. Total recovery was 10.93 g.

Alternative Epoxidation Reaction

To a mixture of benzonitrile (0.80 ml, 7.8 mmol) and potassium bicarbonate in 12 ml of methanol was added [(2-cyclobuten-1-ylmethoxy)methyl]benzene (523 mg, 3.0 mmole) in 12 ml of chloroform followed by the addition of 1 ml of 30% hydrogen peroxide. The mixture was rapidly stirred at room temperature under an argon atmosphere for 92 hours. The reaction was poured into 75 ml of 5% sodium thiosulfate and was extracted with 200 ml of ether. The ether extract was washed with 200 ml of water, 200 ml of saturated sodium bicarbonate and 200 ml of saturated sodium chloride solution. The ether extract was dried over ambydrous sodium sulfate, filtered and the ether removed in vacuo yielding 1.1 grams of crude mixture. The crude material was purified on a 100 ml Merck silica column eluting with 500 ml of hexanes followed by eluting with 1000 ml of 2½% ethyl acetate/hexanes. All fractions containing cis and trans-epoxide were combined. The volatiles were removed in vacuo yielding 478 mg of a 1:2.5 mixture of cis and trans isomers.

(D)
(1α,2β,4β)-2[2-Amino-6-(phenylmethoxy)-9H-purin-9-yl]-4-[(phenylmethoxy)methyl]cyclobutanol Freshly dried (65° C. @ 0.1 mm Hg overnight) o-benzylguanine (1.21 g, 5.0 mmol) and (1α,2α,4α)-2-[(phenylmethoxy)methyl]-5-oxabicyclo[2.1.0]-pentane (571 mg, 3.0 mmol) were dissolved in 13 ml of dry dimethylformamide under an argon atmosphere. 60% Sodium hydride (60 mg, 1.5 mmol) was added to the reaction mixture at room temperature and the reaction was then heated at 110° C. for 3 days. The reaction was cooled to room temperature and the dimethylformamide was evaporated under vacuum at 40° C. yielding the crude product as a brown solid. The residue was partially dissolved in 8 ml of dichloromethane and purified on a 50 ml Whatman LPS1 silica column eluting with 1500 ml of dichloromethane followed by 3000 ml of 2% methanol/dichloromethane collecting 20 ml fractions. The fractions containing pure product were combined and the volatiles removed in vacuo yielding the title compound as a colorless solid, 336 mg.

Alternative Reaction

To a stirring suspension of 2-[(phenylmethoxy)methyl]-5-oxabicyclo[2.1.0]pentane (57.1 mg, 0.30 mmol), o-benzylguanine (121.0 mg, 0.50 mmol, dried for 24 hours at 80° C., 1 mm Hg, over $P_2O_5$), and 18-crown-6 ether (61.0 mg, 0.23 mmol) in sulfolane (1.3 ml, dried over 3A° molecular sieves) at room temperature under argon was added sodium hydride (7.0 mg, 0.175 mmol, 60% oil dispension). After the mixture was heated to 110° C., the solution became homogeneous. After 21 hours at 110° C., the reaction was cooled to room temperature and was quenched with acetic acid (25 ml, 0.4 mmol). Most of the solvent was removed by distillation (0.3 mm Hg) leaaving an orange oily residue. This residue was purified by silica gel chromatography (Merck 230-400 mesh), eluting with $CH_2CL_2$, 1%, 2%, and then 3% MeOM:CH:$CH_2CL_2$ to give the pure coupled product (54.8 mg).

(E)
(1α,2β,3α)-9-[2-Hydroxy-3-(hydroxymethyl)cyclobutyl]guanine (1α,2β,4β)-2[2-Amino-6-(phenylmethoxy)-9H-purin-9-yl]-4-[(phenylmethoxy)methyl]cyclobutanol (336 mg, 0.78 mmol) in 3 ml of dry, distilled tetrahydrofuran was added to 30 ml of liquid ammonia at −78° C. under an argon atmosphere. With stirring, finely cut sodium (165 mg, 6.9 mmol) was added and when the mixture became dark blue in color the cooling bath was removed and the mixture was allowed to stir for 10 minutes. The reaction was quenched by adding small portions of ammonium chloride until the reaction became colorless. The volatiles were next removed by allowing a slow stream of nitrogen to pass through the reaction mixture yielding the crude product as a colorless solid. The crude solid was dissolved in 20 ml of water and the pH was adjusted from pH 12.6 to pH 7.0 by adding 1N hydrochloric acid solution. When the pH reached pH 10 the product began to precipitate from solution. The precipitated product was collected by centrifugation and was washed twice with cold water (2×4 ml). The resulting colorless solid was dried in vacuo overnight at room temperature yielding 134 mg of the title product, melting point 246° (dec.)

Anal. Calc'd. for $C_{10}H_{13}N_5O_3 \cdot 1.25H_2O$: C, 43,74; H, 5.72; N, 25.51. Found: C, 43,43; H, 5.53; N, 25.83.

EXAMPLE 2

(1α,2β,3α)-3-(6-Amino-9H-purin-9-yl)-2-hydroxycyclobutanemethanol (A)
(1α,2β,4α)-2-(2-Amino-9H-purin-9-yl)-4-[(phenylmethoxy)methyl]cyclobutanol A mixture of dried adenine (557 mg, 4.125 mmol) and (1α,2α,4α)-2-[(phenylmethoxy)methyl]-5-oxabicyclo[2.1.0]pentane (523 mg, 2.75 mmol; see example 1C) was partially dissolved in 5.5 ml of dry dimethylformamide under an argon atmosphere. To this mixture was added potassium carbonate (95 mg, 0.69 mmol) followed by 18-crown-6 ether (330 mg, 1.25 mmol) and then the mixture was heated at 110° C. for 50 hours. The reaction was cooled to room temperature, and the volatiles were removed under vacuum at 40° C. yielding the crude product as a brown solid. The residue was partially dissolved in 10 ml of dichloromethane and purifed on a 250 ml Whatman LPS1 silica gel column, eluting with 750 ml of dichloromethane followed by 2000 ml of 2½% methanol/dichloromethane. The fractions containing the pure desired product were combined and the volatiles removed in vacuo yielding the title compound as a colorless solid, 212 mg.

(B)
(1α,2β,3α)-3-(6-Amino-9H-purin-9-yl)-2-hydroxycyclobutanemethanol (1α,2β,4α)-2-(2-Amino-9H-purin-9-yl)-4-[(phenylmethoxy)methyl]cyclobutanol (200 mg, 0.615 mmol) was dissolved in 40 ml of absolute ethanol and 20 ml of cyclohexane. 20% Palladium hydroxide (140 mg) was added and the mixture was heated at reflux for 66 hours. The reaction was filtered through a "milipore" filter to remove the catalyst and the catalyst was washed with approximately 10 ml of ethanol. The volatiles were removed in vacuo yielding the crude product as a colorless solid. The material was dissolved in 5 ml of water and purified on a 50 ml HP-20 column eluting with a 600 ml 50% acetonitrile-water/water gradient. The fractions containing pure product were combined, the acetonitrile removed in vacuo and the water lyophilized to yield 59 mg of product as a colorless solid, melting point 240° (dec.)

What is claimed is:

1. A compound having the formula

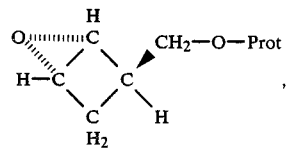

wherein Prot is a hydroxyl protecting group.

* * * * *

UNITED STATES PATENT AND TRADEMARK OFFICE
CERTIFICATE OF CORRECTION

PATENT NO. : 4,855,466

DATED : August 8, 1989

INVENTOR(S) : Robert Zahler & Glenn A. Jacobs

It is certified that error appears in the above-identified patent and that said Letters Patent is hereby corrected as shown below:

TITLE PAGE:

In the Abstract, first formula, left hand side,

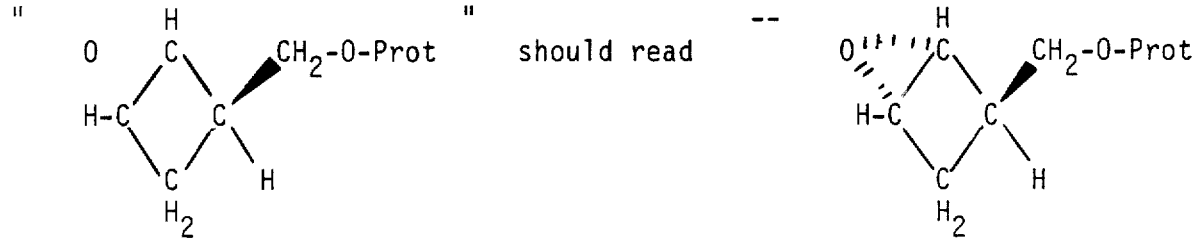

In the Abstract, second formula, right bottom,

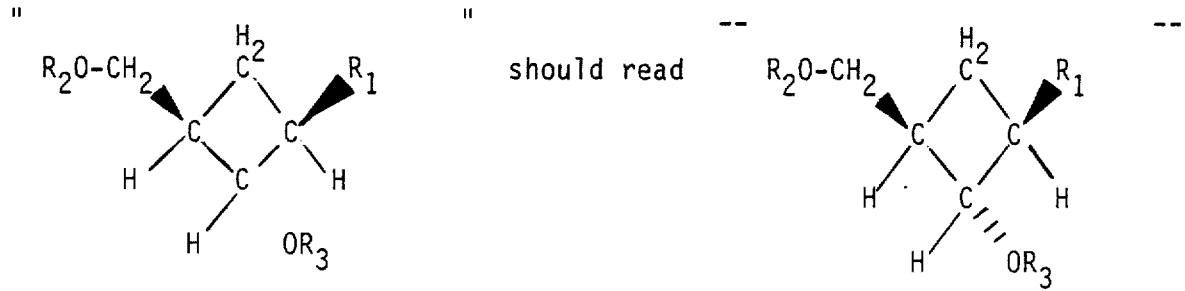

Column 1, line 30,

" wherein $X_1$ "  should read  -- wherein each of $X_1$ --

UNITED STATES PATENT AND TRADEMARK OFFICE
CERTIFICATE OF CORRECTION

PATENT NO. : 4,855,466
DATED : August 8, 1989
INVENTOR(S) : Robert Zahler & Glenn A. Jacobs It is certified that error appears in the above—identified patent and that said Letters Patent is hereby corrected as shown below:

Column 1, line 65
"  The term "acyl"  " should read  --  The term "aryl"  --

Column 4, line 30, formula VIII , left hand side

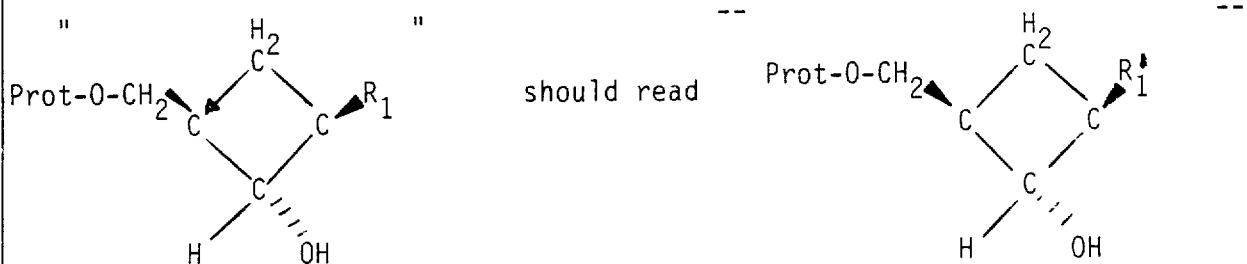

Signed and Sealed this

Fifth Day of November, 1991

*Attest:*

HARRY F. MANBECK, JR.

*Attesting Officer*       *Commissioner of Patents and Trademarks*